United States Patent [19]

Lai

[11] Patent Number: 5,037,963
[45] Date of Patent: Aug. 6, 1991

[54] PROCESS FOR THE PREPARATION OF SYMMETRICAL AZO-DINITRILE, DICARBOXYLIC ACIDS FROM KETO ACIDS

[75] Inventor: John T. Lai, Broadview Heights, Ohio

[73] Assignee: The B. F. Goodrich Company, Akron, Ohio

[21] Appl. No.: 456,901

[22] Filed: Dec. 26, 1989

[51] Int. Cl.$^5$ .................. C07C 245/04; C08F 4/04
[52] U.S. Cl. .................... 534/587; 526/218.1; 526/219; 534/583; 534/586; 534/838; 534/886; 534/887
[58] Field of Search ............... 534/838, 886, 887, 583, 534/586, 587, 578; 256/218, 219

[56] References Cited

U.S. PATENT DOCUMENTS

| | | | |
|---|---|---|---|
| 3,541,132 | 11/1970 | Knowles | 534/586 X |
| 3,783,148 | 1/1974 | Fuchs | 534/586 X |
| 4,028,345 | 6/1977 | Moore, Jr. | 534/58 |
| 4,252,717 | 2/1981 | Wake et al. | 534/838 X |

*Primary Examiner*—Floyd D. Higel
*Attorney, Agent, or Firm*—Daniel J. Hudak

[57] ABSTRACT

The preparation of symmetrical azodinitriles prepared from keto acids is disclosed. A keto acid of the formula

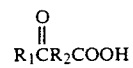

is reacted with $M(CN)_x$ and an ammonia source to obtain an aminonitrile metal carboxylate of the formula

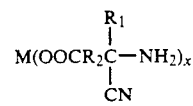

The aminonitrile metal carboxylate is reacted with $M_1(OCl)_x$ with the proviso that no alcohol or surface active agent is utilized to form a metal salt of an azo compound. This metal salt is reacted with mineral acid to give the symmetrical azodinitrile compound of the formula

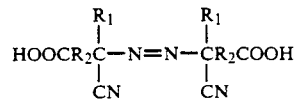

$R_1$ is an alkyl group containing from 1 to about 12 carbon atoms and $R_2$ is an alkylene group containing from 1 to about 12 carbon atoms. M is a metal comprising lithium, sodium, potassium, magnesium or calcium; $M_1$ is a metal comprising sodium, potassium or calcium; and x is the valence of M and $M_1$.

19 Claims, No Drawings

PROCESS FOR THE PREPARATION OF SYMMETRICAL AZO-DINITRILE, DICARBOXYLIC ACIDS FROM KETO ACIDS

FIELD OF THE INVENTION

The present invention relates to an improved process for the preparation of symmetrical azo compounds from keto acids.

BACKGROUND

It is known in the art to prepare azo compounds from a tertiary amine.

U.S. Pat. No. 3,783,148 (Fuchs, Jan. 1, 1974) relates to the preparation of symmetrical azo compounds by the following reaction:

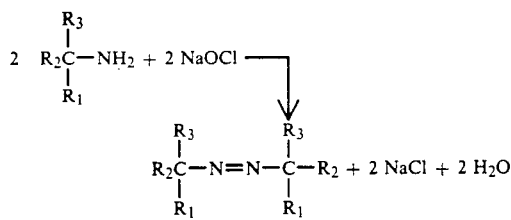

In the above reaction $R_1$ is alkyl of from 1 to about 6 carbon atoms, optionally substituted with an alkoxy group of 1 to about 4 carbon atoms; $R_2$ is cycloalkyl of from 3 to 6 carbon atoms or alkyl of from 1 to 6 carbon atoms; $R_3$ is a radical selected from the group consisting of —CN, —COOR, and —COOM, where R is an alkyl radical of from 1 to 6 carbon atoms, and M is sodium or potassium; with the proviso that $R_1$ and $R_2$ together contain a total of at least 4 carbon atoms, and with the further proviso that $R_1$ and $R_2$ can be taken together and are alkylene of from 3 to 11 carbon atoms. The coupling reaction occurs in the presence of at least 95 percent by volume of a $C_1$-$C_2$ alcohol.

U.S. Pat. No. 4,028,345 (Moore, Jr., June 7, 1977) relates to an improved process for the preparation of aliphatic azo compounds.

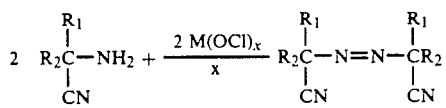

wherein $R_1$ and $R_2$ are selected from the group consisting of aliphatic hydrocarbon radicals of 1 to 8 carbons, optionally substituted with a carboxyl group, a hydroxyl group or an alkoxy group represented by —OR wherein R is an acrylic aliphatic hydrocarbon radical of 1 to 4 carbon atoms; x is the valence of the M ion and a surface active compound selected from the group consisting of an anionic, cationic, nonionic, amphoteric and mixed surface active agents or surfactants. More specifically, this reference relates to a process for the preparation of aliphatic azodinitrile compounds by reacting an aqueous hypochlorite solution with an aminonitrile in the presence of a surface active agent.

The above aminonitriles utilized for the preparation of the azo compounds are prepared in a pressure vessel by reacting a ketone with ammonia gas. The vessel is cooled in a dry ice acetone bath. Hydrogen cyanide is then introduced in portions in an amount equivalent to that of the ketone. The reaction vessel is warmed to room temperature and pressurized to 50 psig with ammonia, heated to 40° C. and 50 psig for 8 hours and cooled to yield an aminonitrile according to the equation below:

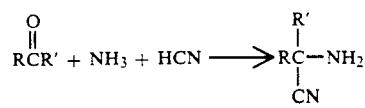

The above references teach the preparation of symmetrical and non-symmetrical azo compounds. In both references, fairly pure aminonitrile is utilized as a starting material for reaction with the metal hypochlorite

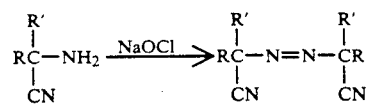

In the past it was thought that an excess of ammonia was to be avoided in the preparation of the aminonitrile since it might interfere with the coupling reaction:

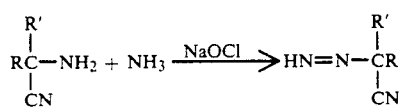

Additionally, water was to be avoided as a solvent in the preparation of the aminonitrile since the water might promote undesirable reverse reactions:

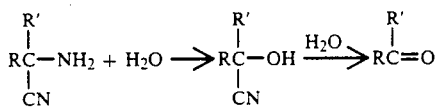

Within the present invention the aminonitrile is formed utilizing a solvent; however, the aminonitrile is not recovered.

SUMMARY OF THE INVENTION

This invention relates to a process for the preparation of a symmetrical azo compound from a keto acid of the formula

wherein $R_1$ is an alkyl group containing from 1 to about 12 carbon atoms and $R_2$ is a direct bond or an alkylene group containing from 1 to about 12 carbon atoms. One mole of the keto acid is reacted with from 1 to about 2 equivalents of $M(CN)_x$ in an aqueous medium wherein M is a metal comprising lithium, sodium, potassium, magnesium, or calcium and x is the valence of M and from 1 to about 2 moles of an ammonia source of ammonium hydroxide (28-30 percent) to form an aqueous solution of an aminonitrile metal carboxylate of the formula

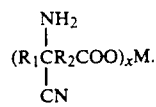

$M(CN)_x$ is not volatile and therefore has none of the deleterious properties of HCN which is used in the commercial production of these initiators.

It is surprising that an aqueous solution that contains excess ammonium hydroxide can be used to give a good yield of an azodinitrile without serious interference with the coupling reaction.

Alternatively, the aminonitrile metal carboxylate can be formed by reacting the keto acid, metal cyanide and ammonia using a lower alcohol as a solvent followed by removal of the alcohol under vacuum. The aminonitrile metal carboxylate so formed, instead of the carboxylic acid as claimed in previous references, is reacted with from about 1.0 to about 2.5 equivalents of $M_1(OCl)$ per mole of keto acid with the proviso that no alcohol or surface active agent is utilized, wherein $M_1$ is a metal comprising sodium, potassium, or calcium to form an azodinitrile metal carboxylate of the following structure:

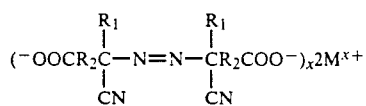

when M is lithium, sodium, potassium, magnesium or calcium and X is the valence of M. The excess $M_1(OCl)_x$ is reduced with a reducing agent comprising sodium bisulfite or sodium sulfite and the metal azo carboxylate is neutralized to form an azodinitrile compound of the formula

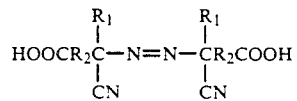

DETAILED DESCRIPTION OF THE INVENTION

The Keto Acid

The keto acids having utility in this invention are of the general formula

$R_1$ is an alkyl group containing from 1 to about 12 carbon atoms, preferably from 1 to about 6 carbon atoms and most preferably from 1 to about 3 carbon atoms. Such groups are known to those skilled in the art. Examples include methyl, ethyl, propyl, isopropyl, butyl, isobutyl and t-butyl.

$R_2$ is an alkylene group containing from 1 to about 12 carbon atoms and preferably 1 to about 6 carbon atoms or a cycloalkylene group containing from 3 to about 12 carbon atoms. When $R_2$ is not cyclic, $R_2$ most preferably contains from 1 to about 4 carbon atoms. When $R_2$ is cyclic it most preferably contains from about 3 to about 6 carbon atoms. Some examples of $R_2$ cyclic alkylenes are

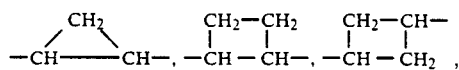

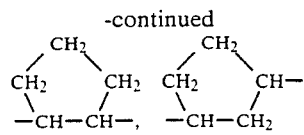

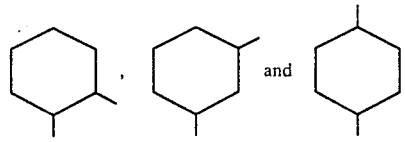

When $R_2$ is not cyclic, examples are methylene, ethylene, propylene, butylene, as well as any branching thereof. The following table lists a few of the many keto acids having utility in this invention. This list is merely illustrative and is not meant to be all-inclusive. A preferred keto acid is levulinic acid.

TABLE I

| | Keto Acids | |
|---|---|---|
| $R_1$ | $R_2$ | Name |
| $CH_3$ | non-existent | pyruvic acid |
| $CH_3$ | $CH_2$ | 3-oxobutanoic acid |
| $CH_3$ | $CH_2CH_2$ | levulinic acid |
| $CH_3$ | $CH_2CH_2CH_2$ | 5-oxohexanoic acid |
| $CH_3$ | $CH_2CH_2CH_2CH_2$ | 6-oxoheptanoic acid |
| $CH_3$ | $CH_2CH_2CH_2CH_2CH_2$ | 7-oxooctanoic acid |
| $CH_3CH_2$ | non-existent | 2-oxobutanoic acid |
| $CH_3CH_2$ | $CH_2$ | 3-oxopentanoic acid |
| $CH_3CH_2$ | $CH_2CH_2$ | 4-oxohexanoic acid |
| $CH_3CH_2$ | $CH_2CH_2CH_2$ | 5-oxoheptanoic acid |
| $CH_3CH_2CH_2$ | $CH_2CH_2$ | 4-oxoheptanoic acid |
| $CH_3$ | $CH_2CH$<br>$\|$<br>$CH_3$ | * 2-methyllevulinic acid |

The Metal Cyanide

One mole of the keto acid is reacted with from about 1 to about 2, preferably 1 to about 1.5, and most preferably from about 1 to about 1.1 equivalents of a metal cyanide of the formula $M(CN)_x$ wherein the metal M comprises lithium, sodium, potassium, magnesium, or calcium and x is the valence of M. An equivalent of $M(CN)_x$ is its weight in grams, pounds, etc. divided by its equivalent weight. The equivalent weight of $M(CN)_x$ is equal to its molecular weight divided by the valence of x. An equivalent weight of NaCN is 49 (49 molecular weight divided by valence of 1) and 49 grams is one gram-equivalent of NaCN. An equivalent weight of $Ca(CN)_2$ is 46 (92 molecular weight divided by valence of 2) and 46 grams is one gram-equivalent of $Ca(CN)_2$. The reaction of the keto acid with $M(CN)_x$ is a reversible addition reaction that strongly favors the right side with very little by-products formed. A preferred metal cyanide is sodium cyanide.

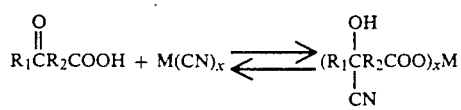

In order to convert the cyanohydrin metal carboxylate to an aminonitrile metal carboxylate, to about 2 moles of an of an ammonia source per 0.5–1 moles of keto acid is introduced.

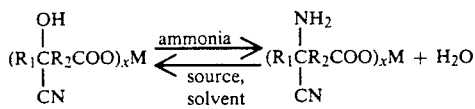 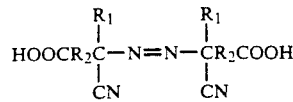

When the ammonia source is ammonium hydroxide (28–30 percent), water is used as a solvent; when the ammonia source is ammonia gas, a lower carbon alcohol is used.

The Metal Hypochlorite

The aminonitrile metal carboxylate is converted to the azodinitrile metal carboxylate by action of $M_1(OCl)_x$ in the ratio of from about 1.0 to about 2.5, preferably from about 1.2 to about 2.0, and most preferably from about 1.2 to about 1.5 equivalents of metal hypochlorite per mole of keto acid. $M_1$ comprises sodium, potassium, or calcium and x is the valence of the metal $M_1$. Sodium is the preferred metal.

Reducing Agent

After the azo compound is formed, the excess unreacted $M_1(OCl)_x$ is removed for environmental concerns. This is done by utilizing a reducing agent such as sodium bisulfite or sodium sulfite. The reducing agent is added as a 20 percent by weight aqueous solution. Further, no alcohol or surface active agent is utilized. Just enough reducing agent is added to provide a negative test for KI-starch test paper; i.e., KI-starch paper is no longer darkened by $I_2$.

or

Neutralization Agent

Once the metal hypochlorite is reduced, the azodinitrile metal carboxylate is ready to be neutralized to form the azo dicyanocarboxylic acid. The neutralization agent is usually an inorganic acid such as hydrochloric acid, nitric acid or sulfuric acid. The preferred mineral acid is hydrochloric acid. The azodinitrile metal carboxylate is of the following structure

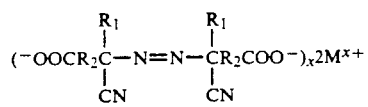

where M is lithium, sodium, potassium, magnesium, or calcium and X is the valence of M. Acidifying the above azodinitrile metal carboxylate yields the azodinitrile of the structure:

$$\begin{array}{cc} R_1 & R_1 \\ | & | \\ HOOCR_2C-N=N-CR_2COOH \\ | & | \\ CN & CN \end{array}$$

The compositions prepared by the process of this invention are formed by preparing a mixture of metal cyanide, ammonia source and solvent. To this mixture is added a keto acid to form the aminonitrile metal carboxylate, $$\begin{array}{c} R_1 \\ | \\ M(OOCR_2C-NH_2)_x \\ | \\ CN \end{array}$$

The order of addition can be varied. It may be carried out as above or the metal cyanide can be suspended or dissolved in solvent, the keto acid added to generate a cyanohydrin followed by the addition of the ammonia source.

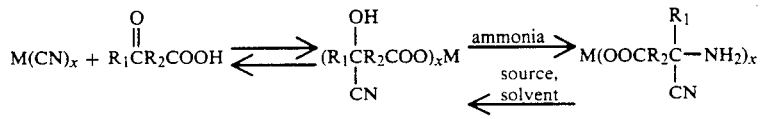

Or the ammonium salt of the acid can be formed first followed by the addition of metal cyanide.

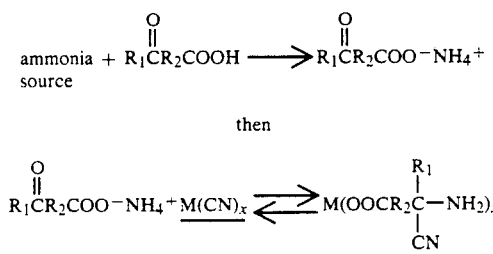

The preferred method is to mix metal cyanide and ammonium hydroxide in water followed by additions of the keto acid. The advantages are (a) the pH is always greater than 8, there is no danger of HCN escaping and (b) all intermediates remain in solution therefore, no solidification can occur.

If excess ammonia is present after the formation of the aminonitrile metal carboxylate, the overall yield of the azodinitrile metal carboxylate is not diminished but rather more metal hypochlorite will have to be used to convert the amino metal carboxylate to the azodinitrile metal carboxylate. The solvent can be water or a lower carbon alcohol such as methanol or ethanol, preferably methanol. If a lower carbon alcohol is used as the solvent, it has to be removed and when this is done, the aminonitrile metal carboxylate is obtained as an oil which tends to solidify. If the lower carbon alcohol is not removed before the addition of the metal hypochlorite, lower yields of azodinitriles are obtained. An advantage of utilizing water as the solvent is that the processing is easier due to the fact that the aminonitrile metal carboxylate does not have to be isolated.

The molar ratio of keto acid:ammonia source is from about 0.5–1:1–2, preferably from 1:1–1.5 and most preferably 1:1–1.1. After reaction of the ammonia source, nitrogen is bubbled through the reaction mixture to remove excess ammonia source. The equivalent ratio of amino nitrile metal carboxylate: $M_1(OCl)_x$ is from about 1:1.0–2.75 preferably 1:1.3–2.0 and most preferably 1:1.5–1.8. The excess $M_1(OCl)_x$ is neutralized with up to about a 100 percent excess of $NaHSO_3$ or $Na_2SO_3$, preferably a 0–10 percent excess and most preferably a 0–2 percent excess of reducing agent. The reaction temperature for any of the intermediates is from about 0° C. to about 60° C. preferably from about 25 to about 50° C. and most preferably from about 30 to about 40° C. The reaction temperature for the coupling of aminonitrile metal carboxylate to form the azodinitrile metal carboxylate is from about −15 to about 35° C., preferably from about 0 to about 25° C. and most preferably from about 0 to about 10° C.

The azodinitrile produced by the process of this invention can be used as a polymerization initiator in emulsion, dispersion and solution polymerization systems. Polymerization involving vinyl chloride, methyl methacrylate, and butadiene-styrene are merely examples of such systems in industry that would benefit from the use of such initiators.

If an azodinitrile containing a low salt content is desired, the azodinitrile can be washed with water either before or after isolation.

The following examples are illustrative of the preparation of azodinitriles. Unless otherwise indicated, all parts and percentages are by weight.

EXAMPLE 1

Charged to a 50 milliliter, three-neck round bottom flask fitted with a thermometer and magnetic stirrer was 5.15 parts (0.105 moles) sodium cyanide, 6 parts water and 6.4 parts (0.105 moles) 28 percent ammonium hydroxide in water. The contents were stirred and cooled in a water bath. At 25° C. 11.6 parts (0.1 mole) levulinic acid dissolved in 7 parts water was added drop-wise. After completion of the levulinic acid addition, the water bath was removed and the temperature was raised to 35° C.

To a 500 milliliter jacketed flask with a thermometer and mechanical stirrer was added 130 parts of a 13 percent aqueous solution of sodium hypochlorite and the temperature was lowered to below minus 5° C. The contents of the 50 milliliter flask were added drop-wise over two hours at a temperature range of between minus 9° C. to minus 5° C. After the addition was complete, 30 parts of a 19 percent aqueous solution of sodium bisulfite were added to reduce the excess sodium hypochlorite. The pH was about 10. An additional 3.2 parts sodium bisulfite solution was added and the resulting pH was 7. Ten parts concentrated hydrochloric acid were added to convert the sodium salt to the free carboxylic acid. The pH was 2. The contents were filtered and the solid product water-washed to obtain 11.2 parts of a white solid having the following structure:

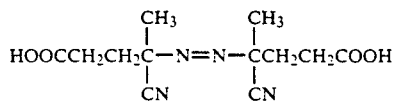

EXAMPLE 2

Added to a one liter three-neck round bottom flask with thermometer and mechanical stirrer was 116 parts (1 mole) levulinic acid and 400 parts methanol. The contents were cooled to 20° C. and 51.5 parts (1.05 moles) sodium cyanide were added in portions. After all the sodium cyanide was added, ammonia gas was bubbled below the surface over a two hour period while maintaining the temperature at 20° C. The contents were stirred at 25° C. for about three hours and filtered and the solid product was rinsed with isopropyl alcohol. About 150.1 parts of a sodium salt of an amino nitrile was obtained.

To a two liter three-neck round bottom flask with thermometer and mechanical stirrer is added 860 parts of a 13 percent aqueous solution of sodium hypochlorite and the temperature is lowered to below minus 5° C. About 150 parts of the sodium salt of the amino nitrile prepared above is dissolved in about 300 parts water and are added drop-wise over a three hour period while maintaining the temperature at between minus 10° to minus 5° C. After this addition is complete, 290 parts of a 19 percent aqueous solution of sodium bisulfite is added to reduce the excess sodium hypochlorite. About 500 parts concentrated HCl is added to convert the sodium salt to the free carboxylic acid. The contents are filtered to give a product having the same structure as in Example 1.

EXAMPLE 3

Charged to a one liter three-neck round bottom flask with thermometer and mechanical stirrer are 51.5 parts (1.05 moles) sodium cyanide, 75 parts water and 64 parts (1.05 moles) 28 percent ammonium hydroxide in water. The contents are stirred and cooled in a water bath. At 27° C., 130 parts (1 mole) 5-oxohexanoic acid is added in a slow stream. After the 5-oxohexanoic acid addition is complete, the water bath is removed and the temperature is raised to 37° C.

To a two liter jacketed flask with a thermometer and a mechanical stirrer is added 573 parts of a 13 percent aqueous solution of potassium hypochlorite and the temperature is lowered to about −5° C. The contents of the one liter flask are added drop-wise at a temperature range of between −10 to −5° C. After the addition is complete, 550 parts of a 19 percent aqueous solution of sodium bisulfite are added to reduce the excess sodium hypochlorite. The pH is at about 10. Nine hundred parts concentrated HCl is added to convert the sodium salt to the free carboxylic acid. The contents are filtered to give a product having the following structure:

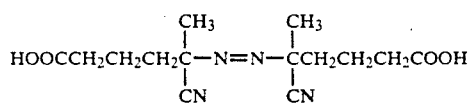

EXAMPLE 4

Charged to a 50-ml, 3-neck, round-bottom flask with thermometer and magnetic stirrer, was 5.15 parts (0.105 moles) sodium cyanide, 17 parts (0.105 moles) 28 percent ammonium hydroxide in water, and 2 parts water. The closed system was cooled in a water bath and at about 35° C. 11.6 parts (0.1 moles) levulinic acid was added drop-wise. The reaction temperature was maintained at between about 35°–40° C. for about 2 hours. The contents were cooled to 25° C. and nitrogen was bubbled below the surface for 1 hour to remove excess ammonia.

To a 300-ml jacketed flask with thermometer and mechanical stirrer was added 74.5 parts (0.14 moles) of the 14.5 percent by weight aqueous solution of sodium hypochlorite and the contents were cooled to about 0° C. The contents of the 50-ml flask were then added drop-wise at between about 0°–5° C. over 52 minutes. After the addition was complete, the contents were stirred for about 1.5 hours at about 0° C. About 5.9 parts of a 20 percent aqueous sodium sulfite solution was added until there was no reaction with KI paper. The pH of the solution was 12. About 40 g water was added followed by 12.5 ml concentrated hydrochloric acid and the pH was lowered to about 1. The contents were filtered and rinsed with 30 ml portions of water three times to give a product having the same structure as in Example 1.

While in accordance with the Patent Statutes, the best mode and preferred embodiment has been set forth, the scope of the invention is not limited thereto, but rather by the scope of the attached claims.

What is claimed is:

1. A process for the preparation of symmetrical azo compounds, comprising, reacting a keto acid

wherein $R_1$ is an alkyl containing from 1 to about 12 carbon atoms, and $R_2$ is a direct bond, or an alkylene containing from 1 to about 12 carbon atoms, or a cycloalkylene containing from about 3 to about 12 carbon atoms with from 1 to about 2 equivalents of $M(CN)_x$ per mole of keto acid wherein M is a metal selected from the group consisting of lithium, sodium, potassium, magnesium, or calcium and x is the valence of M and an ammonia source in a molar ratio of keto acid:ammonia source of from about 1:1–4 in the presence of a solvent to form an aminonitrile metal carboxylate of the formula

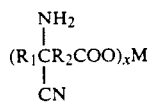

removing excess ammonia source,
removing methanol if used as a solvent, and
reacting said aminonitrile metal carboxylate with from about 1.0 to about 2.5 equivalents $M_1(OCl)_x$ per mole of keto acid with the proviso that no alcohol or surface active agent is utilized with $M_1(OCl)_x$ wherein $M_1$ is a metal selected from the group consisting of sodium, potassium, or calcium and x is the valence of $M_1$ to form an azodinitrile metal carboxylate comprising

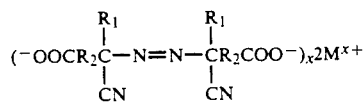

reducing excess $M_1(OCl)_x$ with a reducing agent, and further
neutralizing the azodinitrile metal carboxylate to form

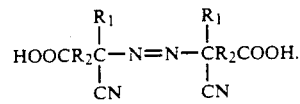

2. The process of claim 1, wherein $R_1$ is an alkyl containing from 1 to about 6 carbon atoms, and $R_2$ is an alkylene containing from 1 to about 6 carbon atoms, or a cycloalkylene containing from about 3 to about 6 carbon atoms.

3. The process of claim 2, wherein the molar ratio of said keto acid to said ammonia source is 1:1–1.5, and wherein the molar ratio of said metal cyanide to said keto acid is 1–1.5:1.

4. The process of claim 3, wherein the molar ratio of said metal hypochlorite to said keto acid is 1:1.2 to 2.0.

5. The process of claim 4, wherein the reducing agent is sodium bisulfite or sodium sulfite in an amount up to about 100 percent excess.

6. The process of claim 5, wherein the azodinitrile metal carboxylate is neutralized with a mineral acid comprising nitric acid, sulfuric acid, or hydrochloric acid, wherein said solvent is water or methanol, and wherein said ammonia source is ammonia or ammonia hydroxide.

7. A process for the preparation of symmetrical azo compounds, comprising, reacting a keto acid

wherein $R_1$ is an alkyl containing from 1 to about 12 carbon atoms, and $R_2$ is a direct bond, or an alkylene containing from 1 to about 12 carbon atoms with from 1 to about 2 equivalents of $M(CN)_x$ per mole of keto acid, wherein M is a metal selected from the group consisting of lithium, sodium, potassium, magnesium, or calcium and x is the valence of M to form a cyanohydrin metal carboxylate of the formula

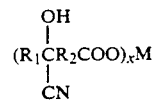

and
reacting said cyanohydrin metal carboxylate with an ammonia source in a molar ratio of keto acid:ammonia source of from about 1:1–4 in the presence of a solvent to form an aminonitrile metal carboxylate of the formula

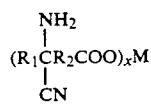

removing excess ammonia source,
reacting said aminonitrile metal carboxylate with from about 1.0 to about 2.5 equivalents $M_1(OCl)_x$ per mole of keto acid with the proviso that no alcohol or surface active agent is utilized wherein $M_1$ is a metal selected from the group consisting of sodium, potassium, or calcium and x is the valence of $M_1$ to form an azodinitrile metal carboxylate comprising

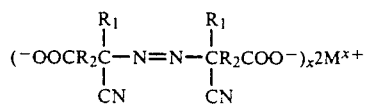

reducing excess $m_1(OCl)_x$ with a reducing agent, and further neutralizing the azodinitrile metal carboxylate to form

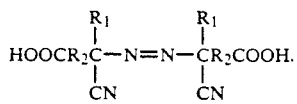

8. The process of claim 7, wherein $R_1$ is methyl and $R_2$ is ethyl.

9. The process of claim 8, wherein M equals sodium.

10. The process of claim 9, wherein the ammonia source is ammonium hydroxide, and the solvent is water.

11. The process of claim 10, wherein the reducing agent is in an amount from about 0 to about 10 percent excess.

12. The process of claim 11, wherein the neutralizing agent is hydrochloric acid.

13. The process of claim 12, wherein the temperature of the reaction for the intermediates is from about 30° C. to about 40° C., and the reaction temperature for the coupling reactions is from about 0° C. to 10° C.

14. The process of claim 7, wherein $R_1$ is an alkyl containing from 1 to about 6 carbon atoms, and $R_2$ is an alkylene containing from 1 to about 6 carbon atoms, or a cycloalkylene containing from about 3 to about 6 carbon atoms.

15. The process of claim 14, wherein the molar ratio of said keto acid to said ammonia source is 1:1–1.5, and wherein the molar ratio of said metal cyanide to said keto acid is 1–1.5:1.

16. The process of claim 15, wherein the molar ratio of said metal hypochlorite to said keto acid is 1:1.2 to 2.0; and
   wherein the reducing agent is sodium bisulfite or sodium sulfite in an amount up to about 100 percent excess.

17. The process of claim 16, wherein the azodinitrile metal carboxylate is neutralized with a mineral acid comprising nitric acid, sulfuric acid, or hydrochloric acid, wherein said solvent is water or methanol, and wherein said ammonia source is ammonia or ammonia hydroxide; and
   wherein $R_1$ is methyl and $R_2$ is ethyl.

18. The process of claim 17, wherein M equals sodium, and wherein the ammonia source is ammonium hydroxide, and the solvent is water.

19. The process of claim 18, wherein the reducing agent is in an amount from about 0 to about 10 percent excess;
   wherein the neutralization agent is hydrochloric acid; and
   wherein the temperature of the reaction for the intermediates is from about 30° C. to about 40° C., and the reaction temperature for the coupling reactions is from about 0° C. to 10° C.

* * * * *